United States Patent [19]
Takahashi et al.

[11] Patent Number: 5,032,714
[45] Date of Patent: Jul. 16, 1991

[54] LIGHT WAVEFORM MEASURING DEVICE INCLUDING A STREAK CAMERA

[75] Inventors: Akira Takahashi; Musubu Koishi, both of Shizuoka, Japan

[73] Assignee: Hamamatsu Photonics K. K., Shizuoka, Japan

[21] Appl. No.: 460,009

[22] Filed: Jan. 2, 1990

[30] Foreign Application Priority Data

Apr. 3, 1989 [JP] Japan .................................. 1-84268

[51] Int. Cl.$^5$ .......................................... H01V 31/50
[52] U.S. Cl. ............................. 250/213 VT; 250/458.1
[58] Field of Search ................. 250/458.1, 461.1, 226, 250/213 R, 213 VT; 356/317

[56] References Cited

U.S. PATENT DOCUMENTS

| | | | |
|---|---|---|---|
| 4,662,748 | 5/1987 | Tanaka et al. | 356/317 |
| 4,786,170 | 11/1988 | Groebler | 250/458.1 |
| 4,895,156 | 1/1990 | Schulze | 250/458.1 |

OTHER PUBLICATIONS

Technical Digest CLEO, '86, WR3 (1986), pp. 230–231.
Sumitani, M. et al., "Channel-Three Decay in Benzene: A Picosecond Fluorescence Investigation", Chemical Physics 93 (1985) 359–371.
Yamazaki, I. et al., "Microchannel-Plate Photomultiplier Applicability to the Time-Correlated Photon-Counting Method", Rev. Sci. Instrum. 56(6), Jun. 1985.

*Primary Examiner*—David C. Nelms
*Attorney, Agent, or Firm*—Finnegan, Henderson, Farabow, Garrett and Dunner

[57] ABSTRACT

Laser sources produce two light beams which are different in frequency and at least one of which is a pulse beam. The two light beams are subjected to sum frequency mixing in a non-linear optical element and a resultant sum frequency beam is applied to a specimen as an exciting pulse beam. A pulse beam separated from the sum frequency beam and synchronized therewith is detected by a photodetector. A measuring means measures a waveform of fluorescence light emitted from the specimen using an output of the photodetector as a measurement starting reference signal. According to one embodiment, the device operates in a single photon counting mode and the measuring means counts repeatedly an elapsed time from the detection of the measurement start reference signal to the detection of the fluorescence light for every divided section of the elapsed time.

7 Claims, 4 Drawing Sheets

LIGHT WAVEFORM MEASURING DEVICE INCLUDING A STREAK CAMERA

BACKGROUND OF THE INVENTION

This invention relates to a light waveform measuring device, which is used to measure, for instance, the life of the fluorescence light which is produced when a laser beam is applied to an object under test.

Examples of conventional light waveform measuring devices having high time resolution are as follows:

A first example of the conventional optical waveform measuring device operates according to the so-called "time correlation single photon counting method". In the method, the photons of fluorescence light emitted from an object under test in response to the application of a light pulse very short in duration time are detected, so that the period of time which elapses from the application of the light pulse until the detection of the photons is measured. In this connection, it should be noted that the device is so adjusted that the number of photons detected per application of the light pulse is not more than one. The time measurement is repeatedly carried out many times (about one million times for high accuracy), and a histogram is formed by using the resultant data, so as to obtain the fluorescence life characteristics of the object under test.

A second example of the conventional optical waveform measuring device employs a streak camera device. The waveform of light emitted from an object under test is measured with a streak tube which performs the sweep of an electron beam in synchronization with the application of a light pulse to the object. By performing the application of the light pulses and the sweep of the electron beam repeatedly the waveform of the light can be measured even when the number of photons emitted from the object is small. In addition, in the case, too, where a number of photons are emitted from the object every application of the light pulse, the light waveform can be measured.

In addition to the above-described devices, a sampling type light waveform measuring device, and devices using a pin photodiode or avalanche photodiode as a photodetector, are known in the art.

In the above-described measurements, it is essential to provide a reference signal for starting a measurement. The light waveform measuring device operating in the single photon counting method cannot operate without a time measurement start signal. The light waveform measuring device with the streak camera cannot operate without a sweep start signal (trigger signal). Therefore, the conventional devices obtain the measurement starting reference signal according to the following two methods: In the first method, the pulse beam from a laser light source is split by a half-mirror or the like into two beams. One of the two beams is applied, as an exciting light beam, to a specimen under test, while the other is applied to a photodetector to obtain the measurement start signal. In the second method, the measurement start signal is obtained by utilizing the signal which is applied to a drive circuit provided for a semiconductor laser constituting a laser light source.

In the first method, however, it is necessary to provide an optical system for splitting the pulse beam into two beams. Accordingly, the light waveform measuring device according to the first method is unavoidably intricate in arrangement. Furthermore, since the pulse beam is split as was described above, utilization of the light beam is not efficient.

In the second method, there arises a drift or jitter between the electrical signal in the drive circuit of the pulse light source and the output pulse beam, so that the relation between timing of the measurement start signal and that of the output pulse beam is not kept constant. Therefore, especially when the counting operation is carried out repeatedly, the timing relation will be shifted every counting operation, with the result that it is difficult to improve the time resolution.

On the other hand, in order to measure the life of fluorescence, it is necessary to use a light beam as an exciting light beam which is shorter in wavelength than the fluorescence light, and laser light source types which can be utilized are therefore limited. In the case of a semiconductor laser which is small in size and can be controlled with ease, it is rather difficult to obtain a laser beam having a short wavelength.

SUMMARY OF THE INVENTION

In view of the foregoing, an object of this invention is to provide a light waveform measuring device simple in construction which can effectively utilize the output pulse beam of a light source and improve the time resolution, and can readily obtain a high-energy (short-wavelength) exciting pulse beam necessary for exciting a specimen under test.

A light waveform measuring device of the invention basically detects light, to measure its waveform, produced from a specimen in response to an exciting light, and has a feature of utilizing a so-called sum frequency mixing. More specifically, the light waveform measuring device, according to the invention, comprises: light sources (such as semiconductor light emitting elements) for outputting first and second light beams which are different in frequency and at least one of which is a pulse beam; mixing means for subjecting the first and second light beams to sum frequency mixing; selecting means for selecting a sum frequency beam from output light beams of the mixing means, which is applied, as an exciting pulse beam, to a specimen; pulse detecting means for detecting a pulse beam which is synchronous with the sum frequency beam from the output light beams of the mixing means; and measuring means for measuring a waveform of light to be measured from the specimen, with an output of the pulse detecting means as a measurement starting reference signal.

The light waveform measuring device may be so modified that the period of time which elapses from the time instant that the pulse detecting means produces the output until the light to be measured is detected is counted repeatedly to measure the light waveform. Furthermore, it may have a streak camera which performs a sweep operation using the output of the pulse detecting means as a trigger signal.

In the optical waveform measuring device of the invention, the measurement starting reference signal is obtained from the pulse beam which is completely synchronous with the exciting pulse beam which is produced by the sum frequency mixing. Therefore, the timing of the exciting pulse beam will not be shifted from that of the measurement starting reference signal by a drift or jitter which may take place in the drive circuit, etc. Furthermore, the exciting pulse beam applied to the specimen is short in wavelength (high in energy), being formed by the sum frequency mixing as was described above.

DETAILED DESCRIPTION OF THE INVENTION

Preferred embodiments of this invention will be described with reference to the accompanying drawings.

Figure 1:
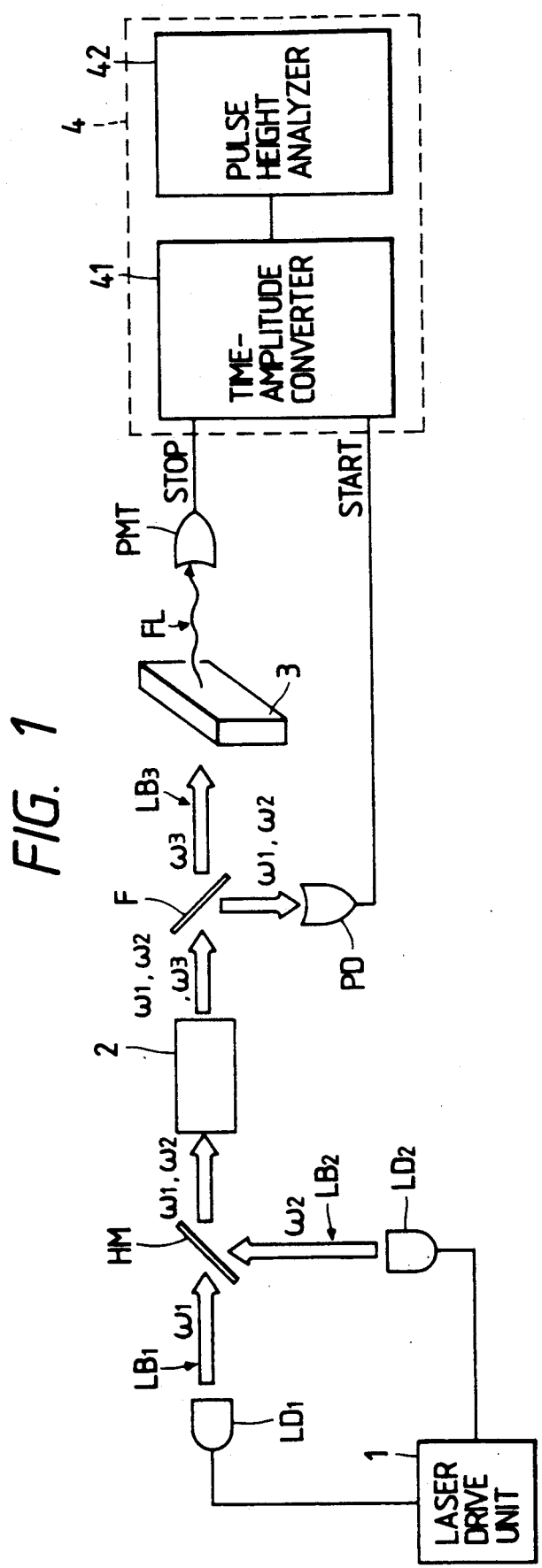
FIG. 1 is an explanatory diagram, partly as a block diagram, showing the arrangement of a light waveform measuring device according to a first embodiment of this invention.

FIG. 1 shows the arrangement of a light waveform measuring device which is a first embodiment of the invention. In FIG. 1, a laser drive unit 1 comprises, for instance, a circuit for outputting an electrical pulse having a predetermined frequency, and a circuit for producing a short pulse current (electrical pulse signal) of several hundreds of picoseconds rising quickly (the circuits being not shown), which is applied to semiconductor lasers $LD_1$ and $LD_2$. In response thereto, the semiconductor lasers $LD_1$ and $LD_2$ produce very short pulse laser beams which have different angular frequencies $\omega_1$ and $\omega_2$ ($f=\omega/2\pi=c/\lambda$), respectively. The very short pulse beam $LB_1$ from the semiconductor laser $LD_1$ meets the very short pulse beam $LB_2$ of the other semiconductor laser $LD_2$ at a half-mirror HM, so that the combination of the very short pulse beams is applied to a non-linear optical element 2. As a result, the non-linear optical element 2 outputs three light beams having angular frequencies $\omega_1$, $\omega_2$ and $\omega_3$ ($=\omega_1+\omega_2$) by sum frequency mixing. Those light beams are applied to a wavelength selecting filter F. The light beam ($\omega_3$) passed through the filter F is applied through an optical lens system (not shown) to an object (specimen 3) under test, so that the specimen 3 outputs fluorescence light FL. The fluorescence light FL thus outputted is detected by a photodetector PMT such as a photomultiplier tube, the detection output of which is applied, as a stop signal, to a stop terminal of a time-amplitude converter 41.

On the other hand, the light beams having the angular frequencies $\omega_1$ and $\omega_2$ reflected by the filter F are detected by a photodetector PD such as a photodiode, the detection output of which is applied, as a start signal, to a start terminal of the time-amplitude converter 41. The time-amplitude converter 41 operates in response to the stop signal and the start signal. The output of the converter 41 is applied to a pulse height analyzer 42.

The time-amplitude converter 41 and the pulse height analyzer 42 constitute measuring means 4 for measuring light waveforms. The measuring means 4 operates as follows:

The light beams having the angular frequencies $\omega_1$ and $\omega_2$ are detected by the photodetector PD, and applied, as the start signal, to the time-amplitude converter 41. The timing of applying the start signal and the timing of irradiating the specimen 3 with the very short pulse beam $LB_3$ provided by the sum frequency mixing are made synchronous with each other. Since the start signal is formed by using the light beams having the angular frequencies $\omega_1$ and $\omega_2$ which contribute to the formation of the specimen exciting very short pulse beam $LB_3$ by the sum frequency mixing, the above-described synchronization will not be affected by the drift or jitter of the drive unit 1.

When the fluorescence light FL (a photon) from the specimen 3 is detected by the photodetector PMT, the output of the latter is applied, as the stop signal, to the time-amplitude converter 41. As a result, the converter 41 produces a voltage pulse whose height is proportional to the period of time which elapses from the time instant that the converter 41 receives the start signal until it receives the stop signal. The voltage pulse is applied to the pulse height analyzer 42. The analyzer 42 converts the voltage pulse to a digital signal, and counts it separately according to the height of the voltage pulse (i.e., counts the number of time periods of that particular duration which have been detected).

Figure 2:
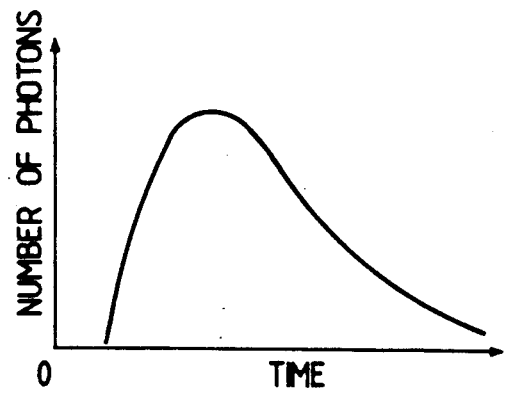
FIG. 2 is a graphical representation showing a result of measurement by the device shown in FIG. 1.

FIG. 2 is a graphical representation indicating one example of the result or distribution of count of the pulse height analyzer 42 in the case where a number of voltage pulses are applied by the time-amplitude converter 41 to the analyzer 42. In the graphical representation, the horizontal axis represents the elapsed time (height of the voltage pulse), and the vertical axis the number of photons. In other words, the vertical axis represents the probability that a photon (fluorescence light FL) is detected at a given time, and therefore the value on the vertical axis is proportional to the intensity of fluorescence at that time. Thus, FIG. 2 indicates the variation in intensity of the fluorescence with time, i.e., the fluorescence life characteristic. In practice, application of the light pulse is carried out one million to several tens of millions times, and the measurement is continued until about one million photons are detected, to determine the life of fluorescence.

The specific features and advantages of the device thus constructed will be described.

First, since the third light beam (sum frequency light beam) formed by the sum frequency mixing is used as the exciting pulse beam applied to the specimen 3, the device can be used for observation of a variety of objects. The principle of generating a sum frequency light beam is described in the publication "Fundamental optoelectronics", pp. 224 to 226. However, it will be briefly described here. When light beams having angular frequencies $\omega_1$ and $\omega_2$ are combined together with a half-mirror or prism, and are then applied to a non-linear optical element such as a non-linear optical crystal (e.g., $LiNbO_3$) or a Cherenkov radiation waveguide type non-linear optical part, a light beam having an angular frequency $\omega_3$ is formed in accordance with the relation:

$$\omega_3 = \omega_1 + \omega_2$$

where $\omega_1 = 2\pi c/\lambda_1$, $\omega_2$, and $\omega_3 = 2\pi c/\lambda_3$.

Therefore, when a laser beam having a wavelength $\lambda_1 = 1.3 \mu m$ is mixed with a laser beam having a wavelength $\lambda_2 = 850$ nm, a sum frequency light beam having a wavelength $\lambda_3 = 514$ nm is provided. The wavelength 514 nm is much shorter (higher in energy) than that (700 to 800 nm) of the ordinary fluorescence light), and therefore the light beam effectively excites the specimen to produce fluorescence light.

Secondly, the measurement reference signal is obtained from the light beams which contribute to formation of the sum frequency light beam, and therefore the time resolution is greatly improved. If one of the semiconductor lasers $LD_1$ and $LD_2$ performs CW light emission, then the other must perform very short pulse light emission, and a sum frequency pulse light beam synchronous therewith is produced. Accordingly, in this case, only the pulse light component obtained by removing the CW light component with a wavelength selecting filter or the like may be detected with the photodetector PD. Alternatively, only the pulse component may be outputted through an AC coupling at the photodetector output, thereby to obtain the above-described measurement reference signal.

Thirdly, the sum frequency light beam of the angular frequency $\omega_3$ is extracted from the output light beam of the non-linear optical element 2 by means of the filter F, and the remaining light beams having the angular frequencies $\omega_1$ and $\omega_2$ are utilized to obtain the measurement reference signal. Therefore, if optical losses at the filter F, etc. are disregarded, then the sum frequency light beam can be used, in its entirety, to excite the specimen 3. Thus, the quantity of light from the light source is used with considerably high efficiency.

Figure 3:
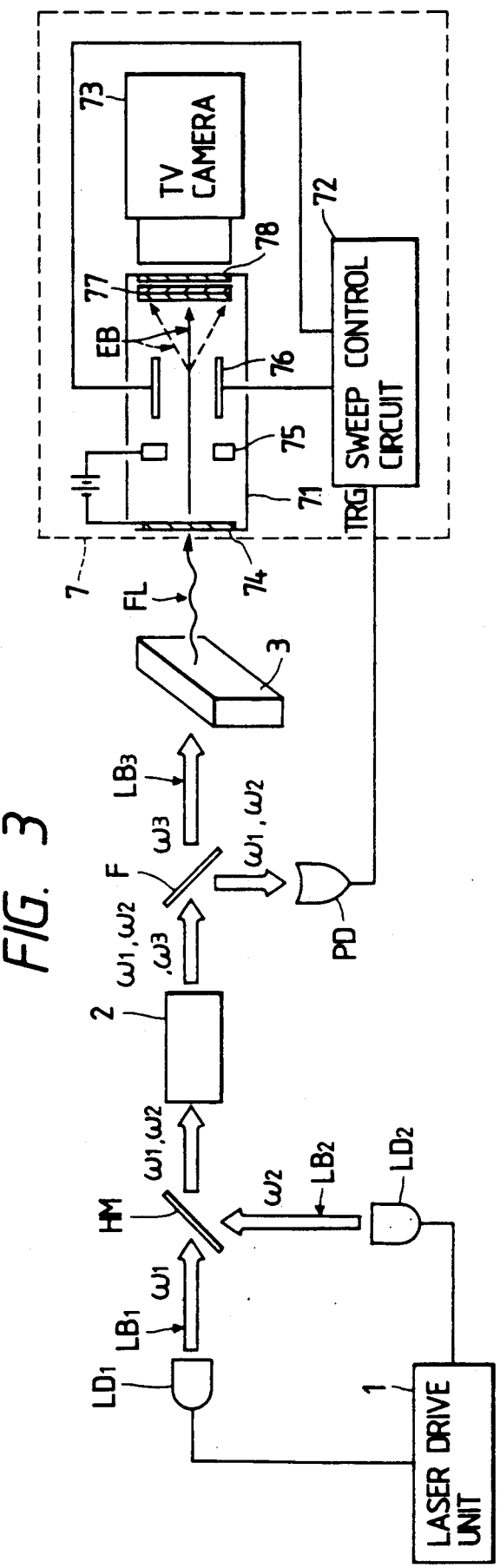
FIG. 3 is an explanatory diagram, partly as a block diagram, showing the arrangement of a light waveform measuring device according to a second embodiment of the invention.

FIG. 3 is an explanatory diagram showing the arrangement of a light waveform measuring device which is a second embodiment of the invention.

The second embodiment is different from the first embodiment in that a streak camera device 7 is employed as its measuring means. The streak camera device 7 comprises: a streak tube 71; a sweep control circuit 72; and a TV camera 73. The streak tube 71 comprises: a photocathode 74 for receiving fluorescence light FL to emit photoelectrons; an accelerating electrode 75 for accelerating electrons emitted from the photocathode 74; a focusing electrode (not shown) for focusing the electrons emitted from the photocathode 74 onto a microchannel plate (MCP); deflecting electrodes 76 for deflecting the accelerated electron beam EB under the control of the sweep control circuit 72; the aforementioned microchannel plate (MCP) for multiplying the number of electrons; and a phosphor screen 78 for receiving the electron beam EB to emit fluorescence light. The streak image formed on the phosphor screen 78 is picked up with the TV camera 73 comprising, for instance, a CCD.

The device of the second embodiment operates as follows. When a sum frequency light beam ($\omega_3$) is produced by output laser beams ($\omega_1$, $\omega_2$) of the semiconductor lasers $LD_1$ and $LD_2$, the laser beams ($\omega_1$, $\omega_2$) synchronous therewith is detected by the photodetector PD and applied, as a trigger signal TRG, to the sweep control circuit 72. The trigger signal is produced by utilizing the laser beam which is completely synchronous with the sum frequency light beam ($\omega_3$) provided as an exciting light beam. Therefore, even if a drift or jitter takes place in the laser drive unit 1, the relation between the timing of inputting the trigger signal TRG and the timing of application of the exciting light beam to the specimen 3 is maintained unchanged. Accordingly, the sweep of the streak camera device 7 is started in synchronization with the application of the very short pulse light beam $LB_3$ having the angular frequency $\omega_3$ to the specimen 3.

When, in the embodiment, a number of photons are emitted, as fluorescence light, in one application of the very short pulse beam $LB_3$ to the specimen 3, a light waveform as shown in FIG. 2 may be observed with one sweep by the sweep control circuit 72. However, if a number of photons are not emitted at a time, the light emission of the semiconductor lasers $LD_1$ and $LD_2$ and the sweep by the sweep control circuit 72 should be repeatedly carried out so that the data of the streak images formed thereby are accumulated. In the first embodiment of FIG. 1, the number of photons produced per application of the very short pulse beam $LB_3$ should be not more than one. However, in the second embodiment, a plurality of photons may be produced per application of the very short pulse beam $LB_3$ because of the use of the streak tube 71.

Figure 4:
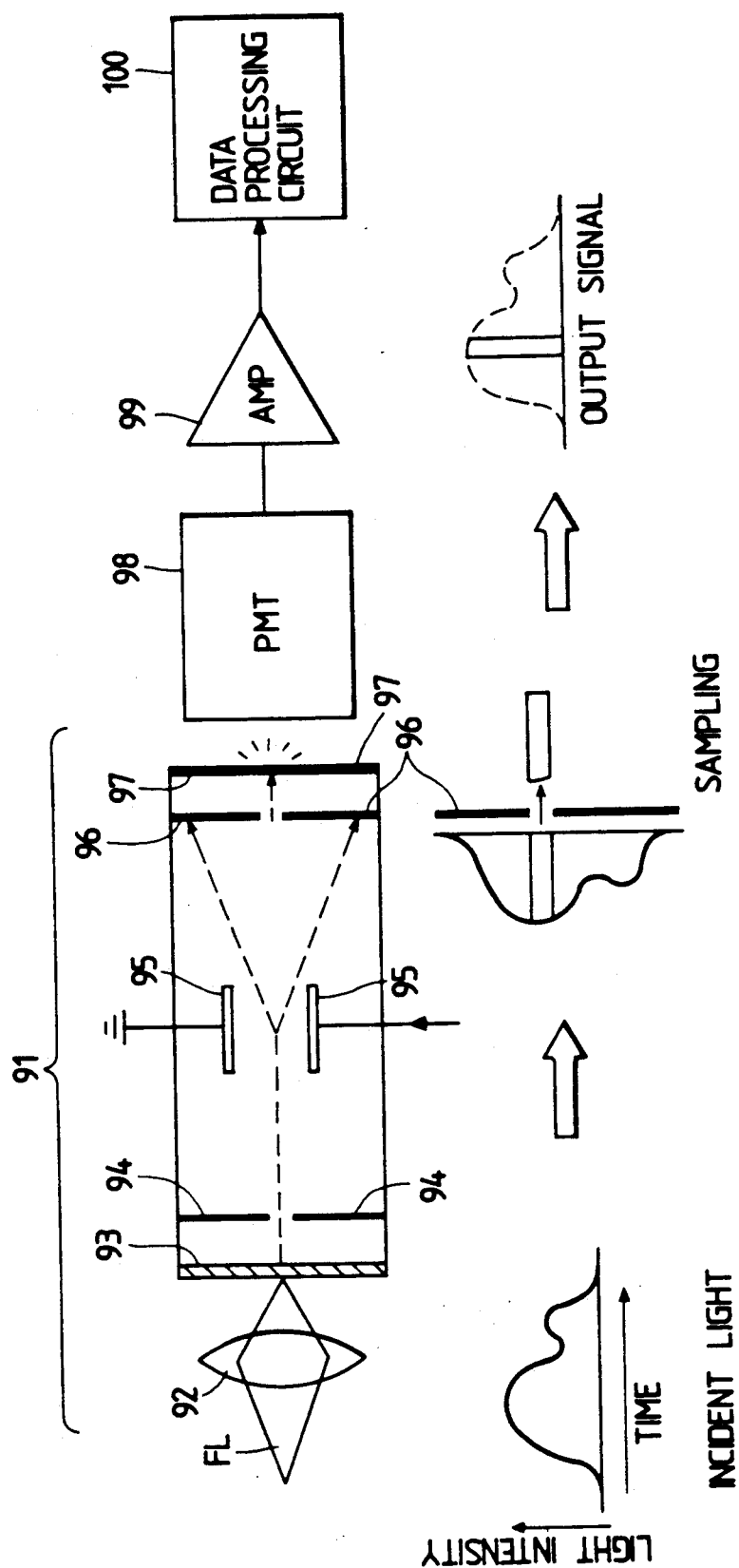

A sampling type light waveform observing means may be employed in place of the streak camera device 7 shown in FIG. 3. The construction and operation of the sampling type light waveform observing means will be briefly described with reference to FIGS. 4 and 5.

The sampling type light waveform observing means essentially comprises: a sampling type streak tube 91; and a data processing section 100 for processing data on the waveform of light FL to be measured which are obtained by extracting part of the light FL with the streak tube 91. The light FL, which is emitted from the specimen and observed by the sampling type light waveform observing means, is focused on a photocathode 93 of the sampling type streak tube 91 by a lens 92. The incident light beam is converted into electrons according to its intensity. The electrons thus produced are accelerated by an accelerating electrode 94, and led through deflecting plates 95 to a slit plate 96. When passing through the deflecting plates 95, the electrons are deflected by a sweep voltage applied between the deflecting plates 95, to reach the slit plate 96. The slit plate 96 has a narrow slit perpendicular to the direction of sweep. Therefore, only part of the electrons pass through the slit to reach a phosphor screen 97 located behind the slit plate 96, thus causing the phosphor screen 97 to emit light. The intensity of the light thus emitted is detected by a photomultiplier tube 98, and amplified by an amplifier 99, which, in turn, produces an electrical signal. The signal obtained by sampling the intensity of the light FL under measurement is stored in the data processing section 100.

Figure 5:
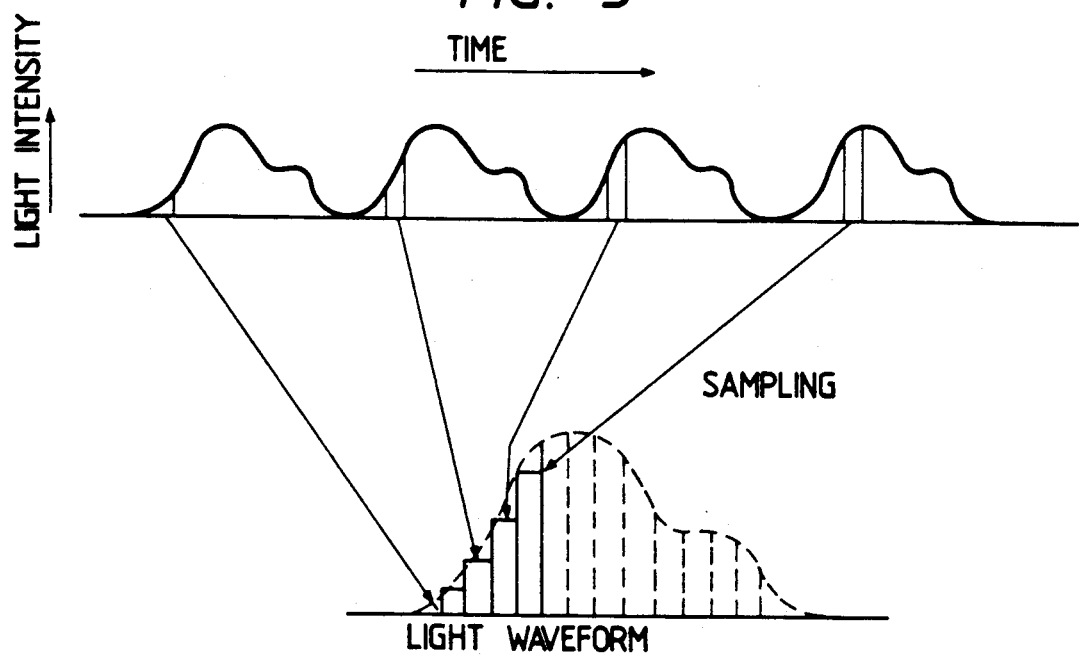
FIGS. 4 and 5 are diagrams for a description of the arrangement and operation of a light waveform measuring device according to a third embodiment of the invention.

The sampling operation is repeatedly carried out with the timing of sweep shifted slightly from that of incidence of the light FL, so that a light waveform as shown in FIG. 5 is obtained from the data obtained by the sampling.

The circuit for outputting the very short pulse current applied to at least one of the semiconductor lasers $LD_1$ and $LD_2$ (an internal circuit of the laser drive unit 1) may employ an avalanche transistor, tunnel diode or step recovery diode, each of which is high in switching speed. Wavelength conversion elements may be provided on the output sides of the semiconductor lasers $LD_1$ and $LD_2$.

As was described above in detail, in the light waveform measuring device of the invention, the reference signal for starting the measurement is obtained from the pulse beam which is completely synchronous with the exciting pulse beam having the sum frequency, and hence a drift or jitter taking place in the drive circuit or the like will never shift the relation between the timing of the exciting pulse beam and that of the measurement starting signal. Since the exciting pulse beam is formed by the sum frequency mixing, the short wavelength exciting beam can be applied to the specimen. Hence, the device of the invention is simple in construction and can utilize the quantity of light of the output pulse beam of the light source with high efficiency, and is high in time resolution. In addition, the device of the invention is applicable to measurement of a variety of objects.

What is claimed is:

1. A light waveform measuring device which measures a waveform of light produced from an object in response to an exciting pulse beam, comprising:
    light source means for outputting first and second light beams which are different in frequency and at least one of which is a pulse beam;
    mixing means for subjecting said first and second light beams to sum frequency mixing;
    selecting means for selecting a sum frequency beam from output beams of said mixing means, and applying said sum frequency beam to said object as said exciting pulse beam;
    pulse detecting means for detecting a pulse beam which is synchronous with said sum frequency beam from said output beams of said mixing means and producing an output when such a pulse beam is detected; and
    measuring means for detecting and measuring said waveform of light produced from said object in response to said exciting pulse beam using said output of said pulse detecting means as a measurement starting reference signal.

2. A light waveform measuring device as claimed in claim 1, wherein said measuring means includes a photodetector for detecting a single photon produced from said object, and said measuring means measures repeatedly a time period which elapses from a time instant that said pulse detecting means produces said output until said photodetector produces an output, to obtain a distribution of said time period as said waveform of light.

3. A light waveform measuring device as claimed in claim 2, wherein said light waveform measuring device is adjusted so as to operate in a single photon counting mode.

4. A light waveform measuring device as claimed in claim 1, wherein said measuring means comprises a streak camera which receives said light from said object to produce photoelectrons and sweeps said photoelectrons using said output of said pulse detecting means as a trigger signal.

5. A light waveform measuring device as claimed in claim 1, wherein said measuring means comprises a sampling type light waveform observing device which receives said light from said object and operates using said output of said pulse detecting means as a trigger signal.

6. A light waveform measuring device as claimed in claim 1, wherein said mixing means comprises a half mirror for combining said first and second light means, and a non-linear optical element for producing said sum frequency beam in response to a combined beam from said half mirror.

7. A light waveform measuring device as claimed in claim 2, wherein said measuring means further includes a time-amplitude converter for converting said time period into a voltage pulse having a height which is proportional to said time period, and a pulse height analyzer for counting said voltage pulse.

* * * * *